US005652098A

United States Patent [19]

Freyer

[11] Patent Number: 5,652,098
[45] Date of Patent: Jul. 29, 1997

[54] METHOD FOR RAPID ISOLATION OF SENSITIVE MUTANTS

[75] Inventor: James P. Freyer, Los Alamos, N. Mex.

[73] Assignee: The United States of America as represented by the United States Department of Energy, Washington, D.C.

[21] Appl. No.: 261,030

[22] Filed: Jun. 14, 1994

Related U.S. Application Data

[63] Continuation of Ser. No. 31,438, Mar. 12, 1993, abandoned.

[51] Int. Cl.$^6$ ...................................................... C12Q 1/68
[52] U.S. Cl. ............................................. 435/6; 435/172.1
[58] Field of Search ............................. 435/172.1, 240.2, 435/6

[56] References Cited

PUBLICATIONS

J. P. Freyer et al. "A New Method For Isolating Radiation-–Sensitive Mutant Cells," Abstracts of Papers for the Fortieth Annual Meeting of the Radiation Research Society, Salt Lake City, Utah (Mar. 14–18, 1992) P–21–10, p. 86.
James P. Freyer et al., "Use of Xantham Gum To Suspend Large Particles During Flow Cytometric Analysis And Sorting," Cytometry 10, pp. 803–806 (1989).
James P. Freyer et al., "Viable Sorting Of Intact Multicellular Spheroids By Flow Cytometry," Cytometry 8, pp. 427–436 (1987).
P. A. Jeggo et al., "X–Ray–Sensitive Mutants Of Chinese Hamster Ovary Cell Line Isolation And Cross–Sensitivity To Other DNA–Damaging Agents," Mutation Research 112, pp. 313–327 (1983).
M. Z. Zdzienicka et al., "Mutagen–Sensitive Cells Lines Are Obtained With A High Frequency In V79 Chinese Hamster Cells," Mutation Research 178, pp. 235–244 (1987).

*Primary Examiner*—James S. Ketter
*Attorney, Agent, or Firm*—Ray G. Wilson; William Eklund; William R. Moser

[57] ABSTRACT

Sensitive mammalian cell mutants are rapidly isolated using flow cytometry. A first population of clonal spheroids is established to contain both normal and mutant cells. The population may be naturally occurring or may arise from mutagenized cells. The first population is then flow sorted by size to obtain a second population of clonal spheroids of a first uniform size. The second population is then exposed to a DNA-damaging agent that is being investigated. The exposed second population is placed in a growth medium to form a third population of clonal spheroids comprising spheroids of increased size from the mammalian cells that are resistant to the DNA-damaging agent and spheroids of substantially the first uniform size formed from the mammalian cells that are sensitive to the DNA-damaging agent. The third population is not flow sorted to differentiate the spheroids formed from resistant mammalian cells from spheroids formed from sensitive mammalian cells. The spheroids formed from sensitive mammalian cells are now treated to recover viable sensitive cells from which a sensitive cell line can be cloned.

6 Claims, 7 Drawing Sheets

Spheroid Diameter (μm)

METHOD FOR RAPID ISOLATION OF SENSITIVE MUTANTS

This is a Continuation of application Ser. No. 08/031,438 filed Mar. 12, 1993, abandoned.

This invention was made with government support under Contract No. W-7405-ENG-36 awarded by the U.S. Department of Energy. The government has certain rights in the invention.

BACKGROUND OF INVENTION

This invention relates to the studies of environmental effects on the health of mammals and, more particularly, to the isolation of mammalian cell mutants that are sensitive to environmental agents.

One area of active research in the environmental field involves the use of mammalian mutant cells that are sensitive to DNA-damaging agents, i.e., environmental agents, e.g., chemical agents, ionizing and ultraviolet radiation, etc. A difficult step in these studies is the initial isolation of a stable, sensitive cell line. In the first instance, only a small number of mutant cells exist in any given cell population. Sensitivity is determined by killing the sensitive cells; yet there must be surviving cells for use in growing a sensitive cell population.

Current technology allows the isolation of only about 500 clones per hour. This means that it takes about 3 months to isolate $10^6$ clones, without even considering the additional time needed to observe the clones for responsive to a given environmental agent. The lack of a rapid and reliable method for screening large numbers of mammalian clones for sensitivity to environmental agents has greatly hindered progress in identifying the genes responsible for DNA damage and repair. For instance, there are about ten laboratories actively involved in isolating the genes responsible for resistance to ionizing radiation; all of this work is concentrated in the study of <20 mutant cell lines. The small number of sensitive mutants available has even precluded the determination of the number of complementation groups for repair or radiation-induced DNA damage, a first step in determining the number of genes involved in this complex cellular activity. Current technology also precludes the isolation and testing of enough mutants to study spontaneous mutations, which are thought to occur at $10^{-6}$ or less in a hemizygous cell line.

The development of a method for rapidly isolating mammalian cell mutants sensitive to environmental agents would have significant application to the study of somatic cell genetics, DNA damage repair, toxicity testing, environmental monitoring, and basic cell biology. The ability to isolate large numbers of sensitive mutants could be used to test mutation induction frequencies, while isolation of many mutants sensitive to a given agent would greatly assist in determining complementation patterns. Isolation of new radiation damage repair mutants may allow a description of the mechanisms of DNA damage repair in mammalian cells. The ability to develop mutants sensitive to a variety of harmful environmental agents would allow sensitive biological testing and monitoring procedures. The isolation of mutants sensitive (or resistant) to hormones and growth inhibitory compounds has proven to be a very powerful technique for developing mechanistic descriptions of basic cellular biology.

Thus, a rapid mutant isolation technique would greatly promote the widespread application of mammalian cell mutants to many areas of genetic and biological research.

Consequently, it is an object of the present invention to provide a method for the rapid isolation of large numbers of individual cell clones.

Another object of the present invention is to provide a method for the rapid identification of putative sensitive clones after exposure to damaging environmental agents.

Yet another object of the present invention is to provide a method for quickly separating sensitive clones from resistant clones.

One other object of the present invention is to provide a method for the recovery of viable cells from sensitive clones after exposure to a selected test agent.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method of this invention may comprise a procedure for isolating sensitive mammalian cell mutants. A first population of clonal spheroids is grown containing both normal and mutant cells. The first population of clonal spheroids is flow sorted to obtain a second population of clonal spheroids of a first uniform size. The second population of clonal spheroids is then exposed to a DNA-damaging agent being investigated. Thereafter, the second population of clonal spheroids is grown to form a third population of clonal spheroids comprising spheroids of increased size formed from the mammalian cells that are resistant to the DNA-damaging agent and spheroids of substantially the first uniform size formed from the mammalian cells that are sensitive to the DNA-damaging agent. The third population of clonal spheroids is flow sorted to differentiate the spheroids formed from resistant mammalian cells from spheroids formed from sensitive mammalian cells.

The spheroids containing the sensitive mammalian cells are then further treated to obtain cell cultures containing sensitive cells. The sensitive cells may then be further exposed to the DNA-damaging agent to better quantify the sensitivity of the cells to the DNA-damaging agent.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings.

DETAILED DESCRIPTION OF THE INVENTION

Figure 1A:
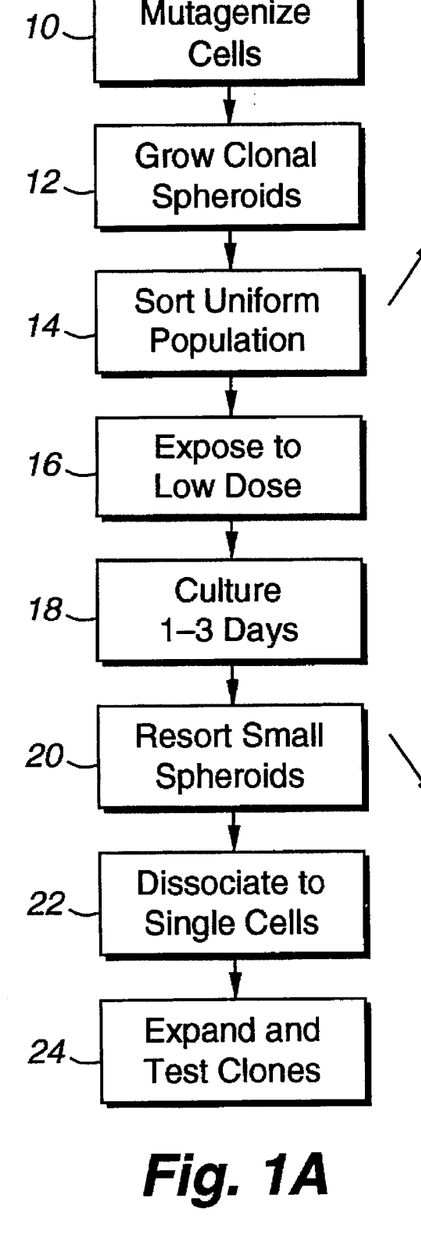
FIGS. 1A, 1B, and 1C pictorially illustrate one embodiment of a process for isolating sensitive mammalian cells according to the present invention.
Figure 1B:
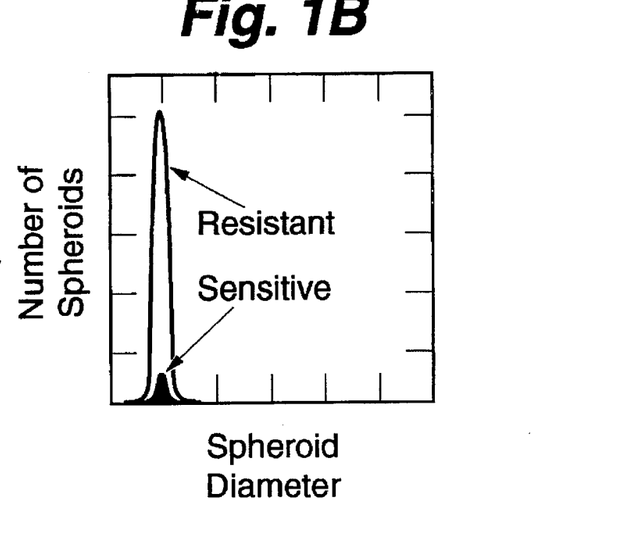
Figure 1C:
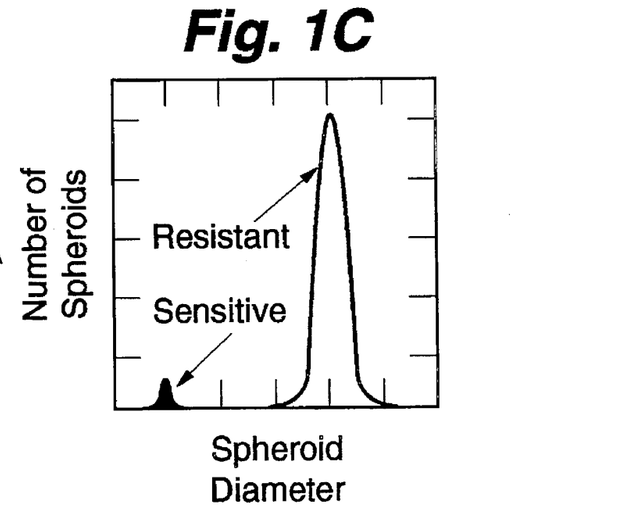

In accordance with the present invention, a method is provided for rapidly screening large numbers of mammalian cell clones for the expression of sensitivity or resistance to a DNA-damaging agent and to quickly separate sensitive or resistant clones for further study. FIGS. 1A, 1B, and 1C pictorially illustrate one embodiment of the method. The method advantageously uses the ability of certain mammalian cell lines to be cultured as spheroids to form spheroid populations with large sizes that can be readily differentiated using the capability of flow cytometry to rapidly sort by size.

FIG. 1A presents a flow chart of one embodiment of a method for isolating sensitive mammalian cells from resistant mammalian cells after exposure to a selected DNA-damaging agent, i.e., ionizing radiation, x-rays, chemical agents, etc. An initial cell population is formed with both wild-type (normal) cells and mutant (sensitive) cells. This initial cell population may be formed from a wild-type cell population that is mutagenized 10 to form a cell population containing both wild-type cells and mutant cells or from naturally occurring cell populations where mutation is not required or is used to enhance the population of mutant cells.

The mutagenized cell population 10 is then plated in agar and clonal spheroids are grown 12 to a convenient diameter, e.g., 50–60 μm containing about 200 cells. The spheroids are then removed from the agar, placed in suspension and flow sorted 14 to produce a first population of clonal spheroids containing both normal and mutant cells. As used hereafter, normal cells are referred to as resistant cells and mutant cells are referred to as sensitive cells to characterize the effect of a selected DNA-damaging agent on the cell line. FIG. 1B graphically illustrates the first population of size-sorted spheroids containing both spheroids of resistant and sensitive cells. Flow cytometry enables the first population to contain spheroids with only a narrow range of diameters.

The first spheroid population is then exposed 16 to a low dose of a DNA-damaging agent that is being investigated. The dose amount is selected to not effect significantly the survival and growth of resistant cells. However, the selected dose amount does kill or arrest the growth of a substantial number of the sensitive cells, yet leaves a small number of the sensitive cells alive.

The exposed spheroids are then returned to a growth medium and cultured 18 for a time effective to continue growing the spheroids containing normal cells. The exposed spheroids containing sensitive cells do not increase substantially in size during this growth period since the DNA-damaging agent has slowed or completely stopped the growth of the sensitive cells. After several days in culture, the spheroid population is again flow sorted 20 with at least one sort window set to select spheroids that are near the size initially sorted to a uniform population 14.

The size divergence of the spheroids containing resistant cells and the spheroids containing sensitive cells subpopulations after the additional growth in culture 18 is shown in FIG. 1C. The isolated spheroids containing sensitive cells may be further examined for sensitivity to the DNA-damaging agent since some live cells remain in the spheroids. The surviving potential mutants in the sorted spheroids can be cultured in situ as is done commonly for radiobiological assays, or the individual cells can be dissociated 22. The cell clones obtained from these sensitive spheroids may then be expanded 24 to provide a sensitive cell line for use in further investigation of the DNA-damaging agent under investigation.

The following protocols are used to implement the procedure depicted in FIG. 1A. The protocols are directed to use with CHO cell lines, CHO-K1 (a resistant cell line) and CHO-XRS6 (a sensitive cell line), to demonstrate the efficacy of the process with known cell lines. However, the procedure is only limited by the requirement for the cell lines to be cultured as spheroids. Such cell lines include, however, most commonly used mammalian cells, CHO and V79 as well as a wide variety of other cell types. See, e.g., R. M. Sutherland, 240 Science, pp. 375–384 (1989); J. P. Freyer, 48 Cancer Res., pp. 2432–2439 (1989). Another limitation on the choice of cell lines is that the DNA-damaging agent does not produce an actual decrease in spheroid size or not cause spheroid dissociation. It has been shown that ionizing radiation does not cause this problem and it is not believed to be a problem for UV radiation and most DNA-damaging drugs. Further, there should not be a large divergence in growth rates among the mutagenized spheroid population. These characteristics are readily determined by routine laboratory tests and the invention is not limited to the specific cell lines set out in the protocols.

Protocols

Cell Mutagenization

A population of a selected cell line can be mutagenized by any number of well known laboratory techniques to produce a population of mutant cells among wild-type cells or to enhance a native population of mutant cells. By way of example, treatment of a population of CHO-K1 cells for 24 hours with 300 μg/ml ethyl methanesulphonate produces mutant cells that are sensitive to a variety of DNA-damaging agents. See P. A. Jeggo et al., "X-ray-sensitive Mutants of Chinese Hamster Ovary Cell Line Isolation and Cross-sensitivity to Other DNA-damaging Agents," 112 Mutat. Res., pp. 313–327 (1983). In some instances the selected cell population may contain sufficient mutants for use without mutagenization or it may be desired to examine only the native mutant cells such that the mutagenization step may be omitted.

Growth of Clonal Spheroids

Spheroids are cultured and grown from individual cells of CHO-K1 and CHO-XRS6. A single cell suspension of approximately $10^7$ total cells is prepared from the mutagenized population using standard cell culture techniques. The cell suspension is then mixed with an equal volume of a 0.2% solution of liquified agarose in culture medium at 37° C., to yield a suspension of cells in 0.1% agarose. The agarose cell suspension is then placed into standard tissue culture dishes and solidified by cooling. This results in a dispersed population of individual cells suspended in the semi-solid agarose. The suspended cells then grow, forming spheroidal colonies (hereinafter referred to as "spheroids") within the agarose, each derived from an individual cell. See J. P. Freyer, 8 Cytometry, infra.

For CHO cells to attain a population of spheroids with a mean diameter of about 75 µm, with each spheroid containing an average of about 100 cells, a time of 4–5 days in culture is required. A low gelling temperature agarose permits individual spheroids to be recovered by remelting the agarose and collecting the spheroids by centrifugation.

Figure 2:
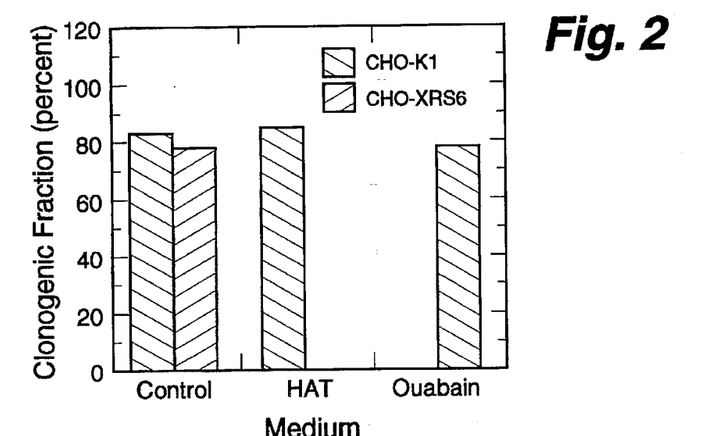
FIG. 2 graphically illustrates a capability to provide controlled populations of resistant (CHO-K1) and sensitive (CHO-XRS6) cells for demonstrating the present invention.

These spheroids maintain their clonal nature during culture and after separation from a mixture even when the original single cell suspension dispersed in the agarose is a 50:50 mix of these two cell lines. This clonal separation is shown in FIG. 2, which shows that spheres resistant to HAT contain only CHO-K1 and no CHO-XRS6 and spheres resistant to Ouabain contain only CHO-K1 and no CHO-XRS6. It will be appreciated that about $10^6$ individual spheroids of CHO cells have been cultured in 30 ml of 0.1% agarose-containing medium in one 100 mm dish without cross-contamination of cells between clonal spheroids; $10^8$ spheroids can readily be cultured in a suitable number of dishes. It has been shown that spheroids can be grown from a number of different CHO and V79 cell lines and that spheroids of the CHO-K1 and CHO-XRS6 cell lines grow at the same rate.

Sorting of Intact Spheroids

Figure 3A:
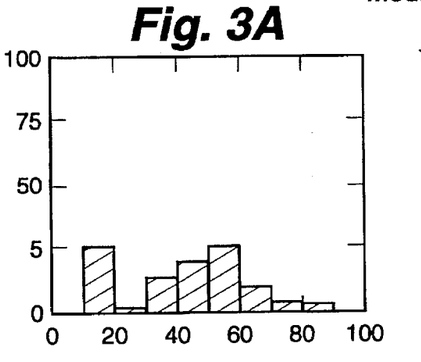
FIGS. 3A, 3B, 3C, and 3D graphically illustrate the capability of flow sorting to provide uniform spheroid size populations.
Figure 3B:
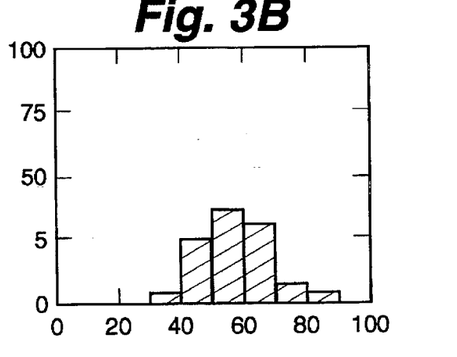
Figure 3C:
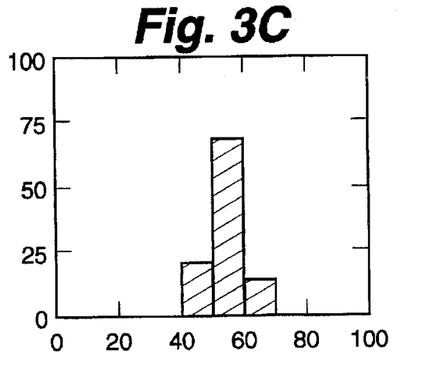
Figure 3D:
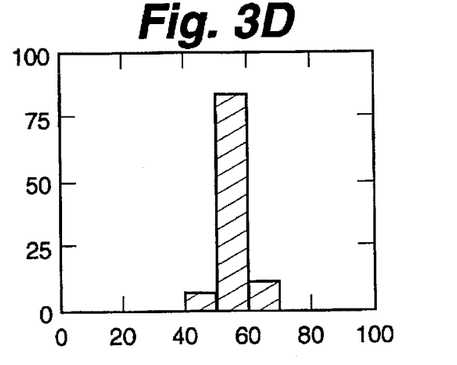

The spheroids recovered after the additional growth period have a relatively large variation in sizes (diameter coefficient of variation about 30%) due to differences in growth rates of the individual cells. A more uniformly-sized population is then obtained by sorting this spheroid population. The flow sorting by size of intact spheroids up to 100 µm in diameter is known. See, e.g., J.P. Freyer et al., "Viable Sorting of Intact Multicellular Spheroids by Flow Cytometry," 8 Cytometry, pp. 427–436 (1987); J. P. Freyer et al., "Use of Xantham Gum to Suspend Large Particles During Flow Cytometric Analysis and Sorting," 10 Cytometry, pp. 803–806 (1989), both incorporated herein by reference. Populations of greater than $10^5$ spheroids with a diameter coefficient of variation less than 5% can be recovered in less than an hour. FIGS. 3A–3D graphically illustrate the uniformity of spheroid diameters obtained in a flow sorted sample (FIGS. 3C and 3D) to select spheroids having a diameter of 50–60 µm from a spheroid population having spheroid diameters in the range 10–90 µm (FIG. 3A). By way of comparison, a screen sorted population (FIG. 3B) does not exhibit the population size uniformity shown for flow sorting.

Figure 4A:
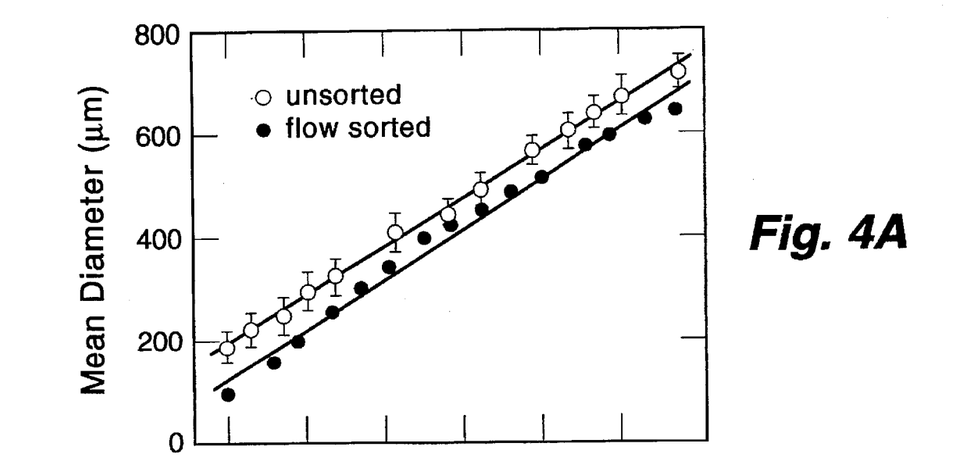
FIGS. 4A and 4B graphically illustrate that flow sorting does not effect the rate of spheroid growth and that the size distribution remains small during growth after sorting.
Figure 4B:
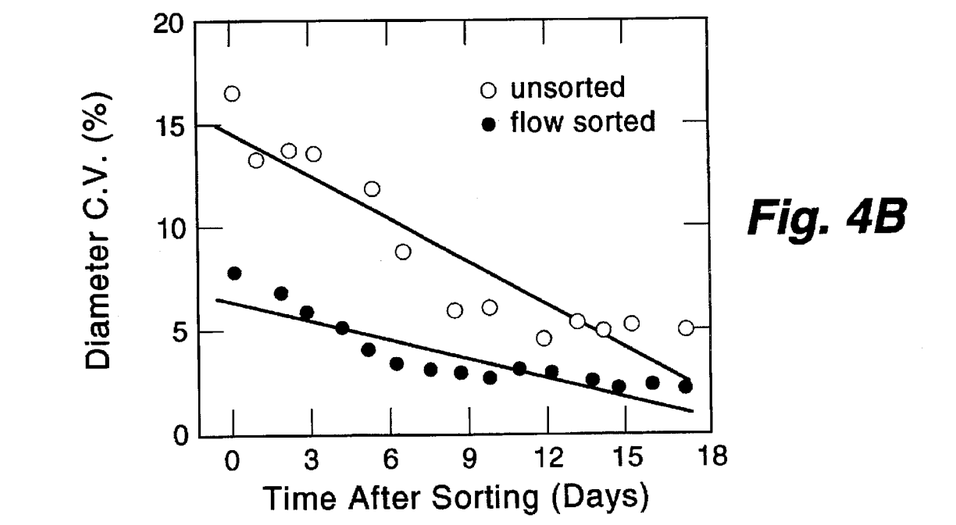
Figure 5:
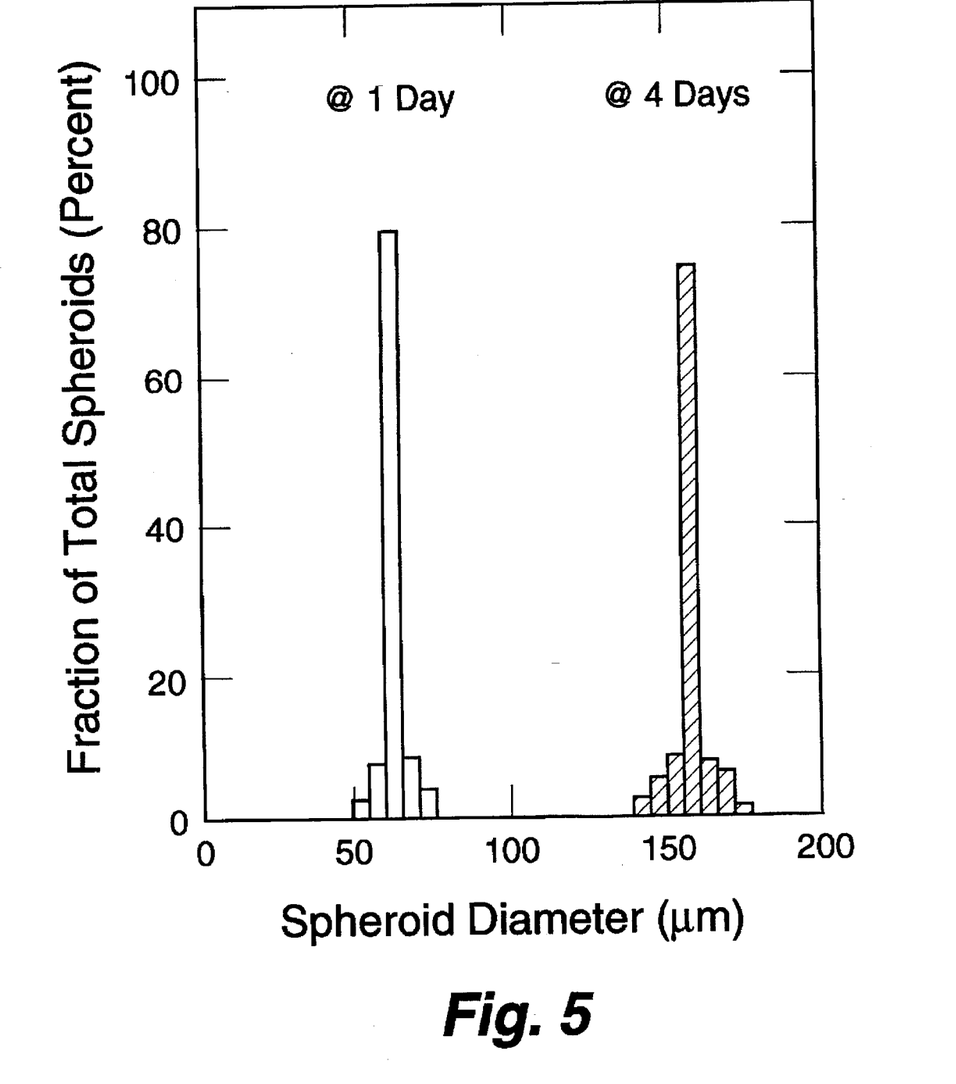
FIG. 5 graphically illustrates that the growth of spheroids containing normal cells provides adequate differentiation from spheroids containing sensitive cells.

Further, the growth rate and size uniformity of the wild-type CHO spheroids produced in subsequent growth of the sorted spheroids was unaffected. These characteristics are shown in FIGS. 4A and 4B, respectively, and demonstrate that additional culture will increase the size of spheroids formed of wild-type/resistant cells to clearly differentiate from sensitive cells that do not grow substantially after exposure to a DNA-damaging agent. FIG. 5 illustrates the increase and complete separation of spheroid sizes after 3 additional days of culture for spheroids containing resistant cells.

While flow separation is the preferred technique to obtain populations of uniformly sized spheroids, other techniques may be used, provided that a sufficiently large population of spheroids is available. Conventional size separation techniques such as gradient centrifugation or unit-gravity sedimentation may also be used.

Slower Spheroid Growth After Exposure

The first step in selecting the mutants of interest is to expose the entire sorted population to a low dose of radiation. For those spheroids derived from cells with the resistant radiation response, this dose will have little effect while spheroids formed from mutant cells that are sensitive to radiation will be greatly affected by the radiation. The effect on the sensitive cells has two manifestations: (1) a delay in progression through the cell cycle for all of the cells; and (2) proliferative cell death for some fraction of the cells. Together, these effects of radiation on the spheroids composed of radiation-sensitive mutants result in markedly reduced growth rate.

Figure 6:
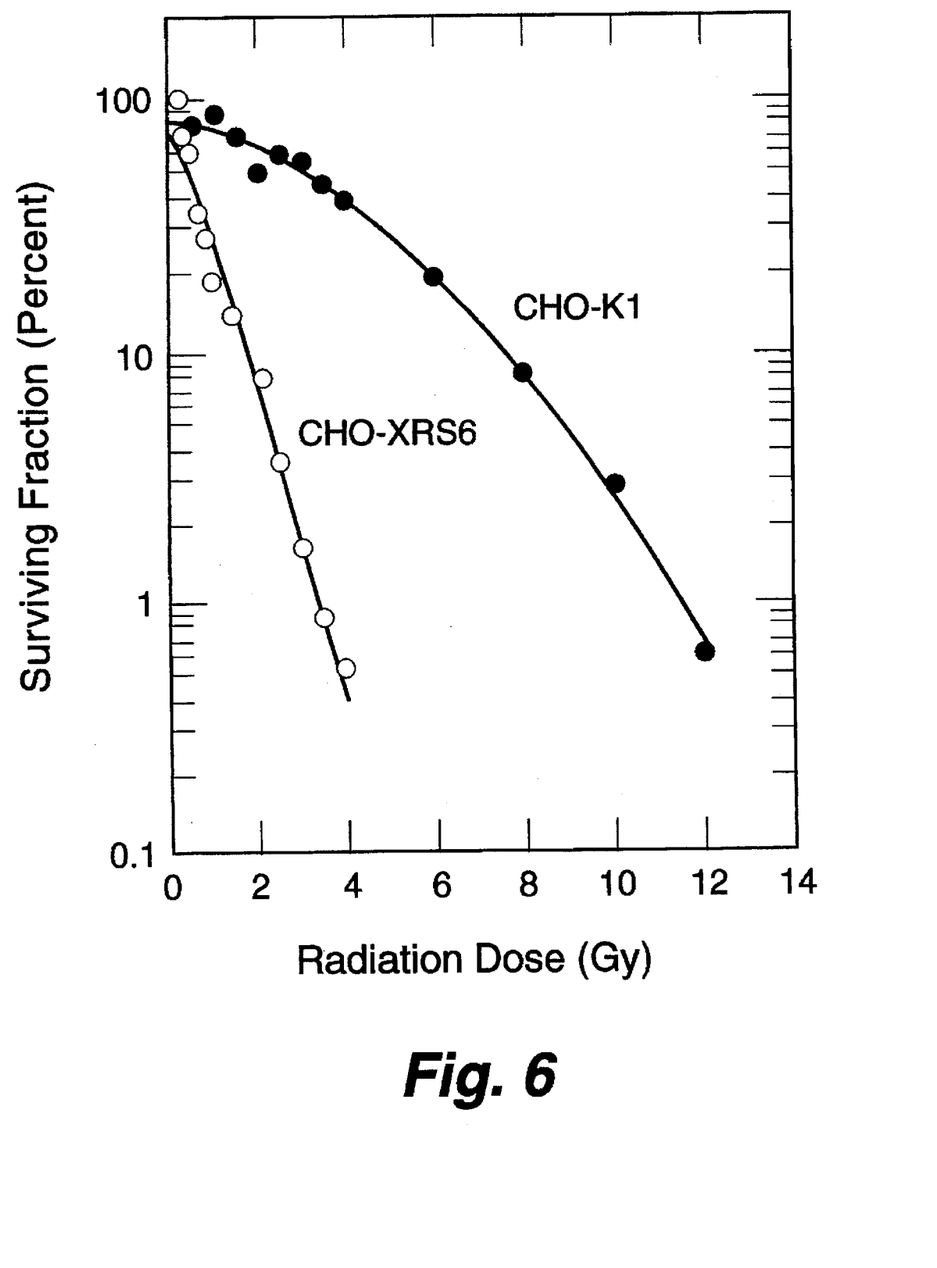
FIG. 6 graphically indicates the relative sensitivity to ionizing radiation of CHO-K1 and CHO-XRS6 cell lines.

Irradiating spheroids from CHO-K1 and CHO-XRS6 cell lines with ionizing radiation to a dose of about 2 Gy left surviving cell fractions of 80–90% and 5%, respectively, as shown in FIG. 6. The irradiated spheroids containing the CHO-XRS6 cell line had no spheroid growth for 3–5 days after the irradiation. Neither of the CHO cell lines exhibited any significant decrease in spheroid size or any shedding of cells from the spheroid surface. The data further indicated that the irradiated spheroids remained clonal in nature even though they were co-cultured in suspension.

Differentiation of Sensitive Cells

In order to detect the differentiating effects of the low dose of radiation, the sorted population of spheres is returned to suspension culture after exposure. The spheroids are maintained in culture for a sufficient period to allow the resistant population to increase in diameter 2–3 fold. For CHO cells, this growth differentiation occurs in 2–3 days.

Figure 7:
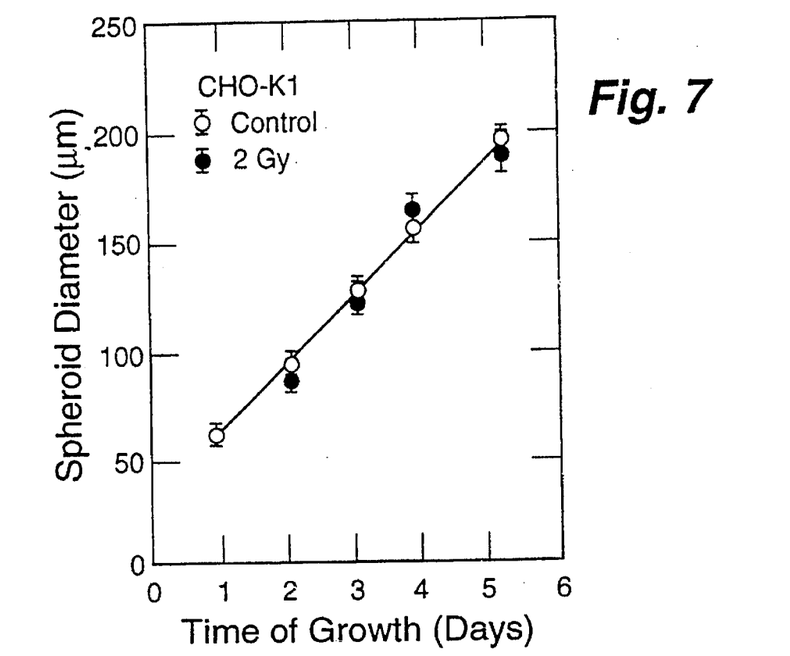
FIG. 7 graphically illustrates that the growth of spheroids containing CHO-K1 (normal) cells is not affected by low-dose radiation.
Figure 8:
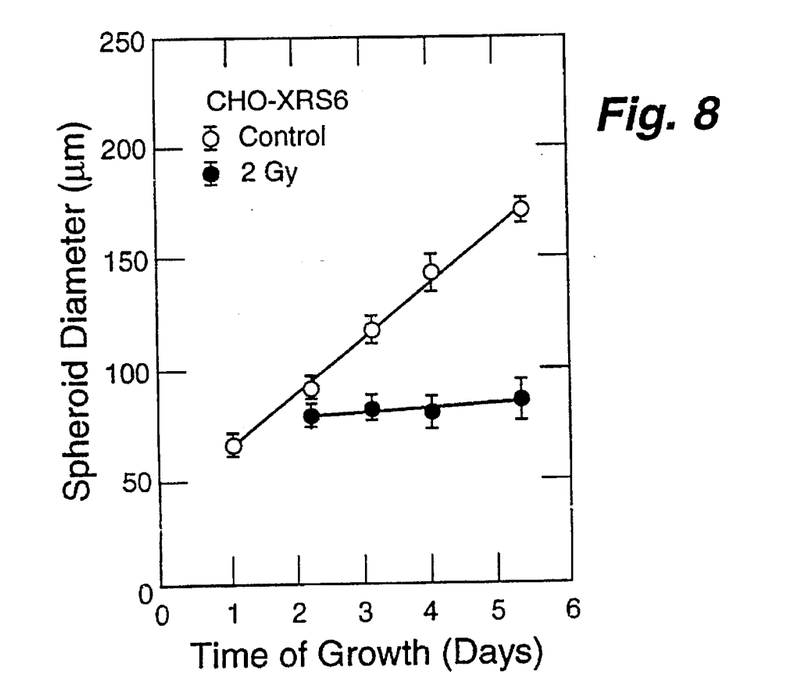
FIG. 8 graphically illustrates that the growth of spheroids containing CHO-XRS6 (sensitive) cells are severely retarded by low-dose radiation.

FIG. 7 shows that the growth of the CHO-K1 spheroids was not affected by a radiation dose of 2 Gy. FIG. 8 shows that the growth of the sensitive CHO-XRS6 spheroids was severely retarded by the low-dose radiation of 2 Gy. In both instances, the spheroid size distribution remained uniform during growth in culture after irradiation.

Resort Individual Spheroids

In order to separate the sensitive spheroids from the resistant spheroids, the population is again analyzed and sorted using a flow cytometer adapted for large particles (J.P. Freyer et al., 8 Cytometry, supra). The flow sort window is adjusted to sort out those spheroids in the mixed population that have not significantly increased in diameter during the culture period following radiation exposure. In the case of the CHO mixture, resistant spheroids grew from about 50 µm in diameter to about 150 µm in diameter three days after exposure to 2 Gy of radiation. The diameter of the sensitive spheroids did not substantially increase. The separation between the radiation sensitive and resistant spheroids was much larger than the size variation within each subpopulation, allowing easy flow sorting of the smaller subpopulation.

Figure 9:
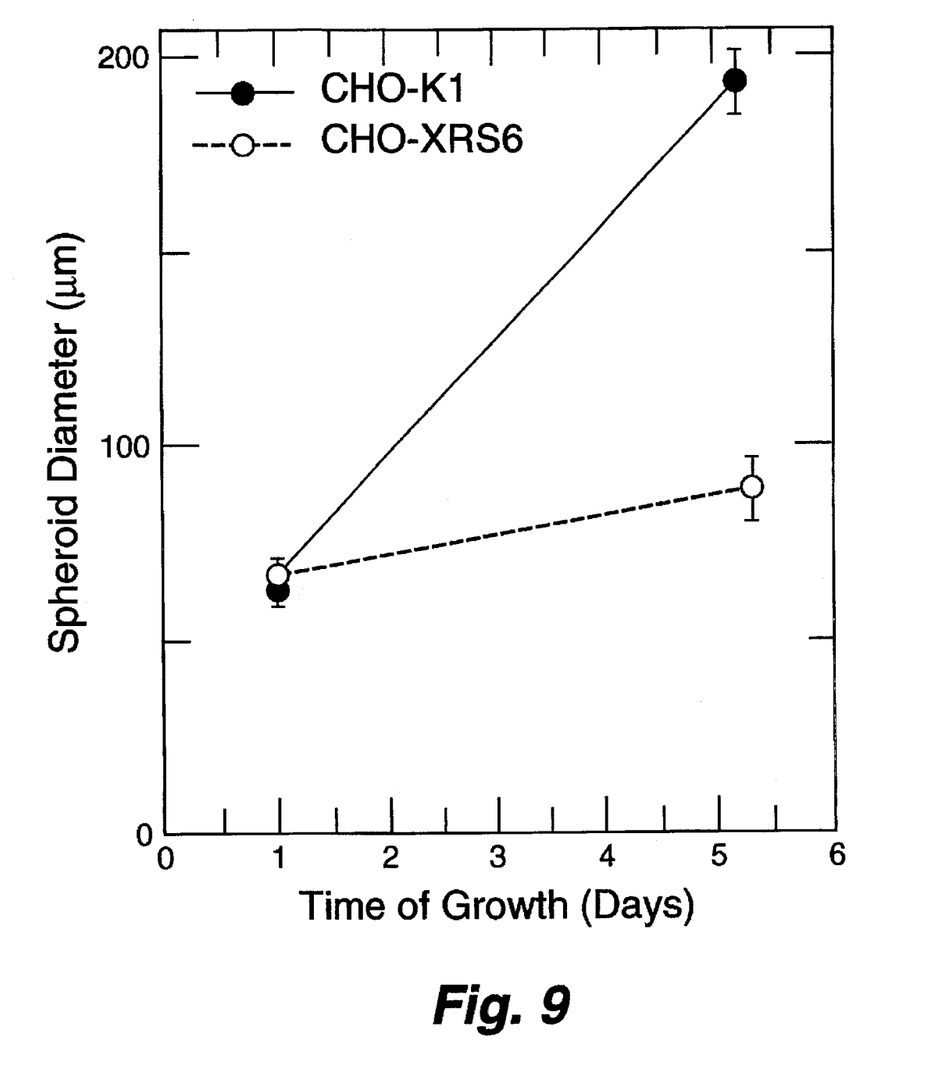
FIG. 9 graphically illustrates the divergence in growth of spheroids containing sensitive and resistant spheroids after low-dose radiation.

FIG. 9 graphically depicts the relative growth of CHO-K1 cells and CHO-XRS6 cells after exposure to ionizing radiation. Thus, subsequent flow sorting of the irradiated and re-cultured spheroid population readily separates the resistant CHO-K1 spheroids from the sensitive CHO-XRS6 spheroids.

Dissociate Individual Spheroids to Single Cells

In order to recover the radiation-sensitive mutants for further study, the spheroids sorted from the non-growing population are dissociated by standard trypsinization to a population of single cells. Each non-growing spheroid is placed (or flow sorted directly) into a single well of a standard multi-well dish, and dissociated individually using a procedure for dissociating individual monolayer colonies. A conventional technique uses a sterile wooden toothpick to pick up and transfer the individual cells. See, e.g., P. A. Jeggo, 112 Mutat. Res., infra.; M. Z. Zdzienicka, "Mutagen-sensitive Cell Lines Are Obtained with a High Frequency in V79 Chinese Hamster Cells," 178 Mutat. Res., pp. 235–244 (1987). The resulting cell suspensions are each derived from a unique clone that is sensitive to radiation.

Expand Clone from Surviving Cells

As a last step, the cell suspensions derived from each selected spheroid are cultured in order to expand the clone for further characterization and use. It has been demonstrated that viable cells then can be recovered from radiation-exposed spheroids of the CHO-XRS6 cell lines after a dose of radiation that reduced the surviving fraction to 5% and that radiation-exposed spheroids can regrow in situ even when there was an average of one surviving cell per spheroid. This permits the separated CHO-XRS6 spheroids to provide isolated sensitive cells for use in cloning a population of the sensitive cells for further investigation involving the DNA-damaging agent used to initially affect the sensitive cell line.

The process herein described has significant advantages over current processes for mutant isolation. A primary advantage is that the procedure for initially selecting the spheroids and for analyzing the exposed population for the presence of sensitive mutants is very rapid. Flow cell sorting of viable, intact spheroids has been demonstrated at analysis rates up to 200 spheroids per second wherein a population of $10^6$ uniformly-sized spheroids could be selected in 6–7 hours. Since the second sort to isolate slow-growing clones involves the selection of rare events, the sort rate is limited by the analysis rate and the same population of spheroids could be screened in a little over an hour.

The increased speed is particularly useful in identifying the few sensitive clones. This is currently done by manual observation of colony sizes; even a specially-designed piece of equipment only analyzes several thousand colonies per day. It will be appreciated that a flow cytometer should be equipped to sort large particles to support spheroid sorting. This capability is described in J. P. Freyer, 8 Cytometry, supra.

Another advantage is that the initial selection of a uniformly-sized population should virtually eliminate the contamination of the screened population by mutagenized cells with a slow-growth phenotype that is independent of exposure to the DNA-damaging agent, since such spheroids would not be selected in the initial sort. The fact that the sorted sensitive spheroids contain approximately 200 cells is also an advantage since surviving cells are expected in the exposed spheroids. Even after an exposure that kills 99% of the sensitive clones, there would be one or two surviving cells.

One other advantage is that the assay used for differentiating sensitive from resistant clones is unambiguous; the incubation time between exposure to the test agent and the second sort can be adjusted such that the probability of finding a resistant spheroid retaining the original diameter would be less than $10^{-5}$. Finally, the procedure results in a significant reduction in the use of culture plates and medium for maintaining the cultures. For example, a typical replica plate used for screening clones for sensitivity contains at most 400 colonies; one would need a minimum of 2500 dishes to culture $10^6$ colonies for observation by this method. Spheroids can be grown much denser and kept separate by suspension in agar.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for isolating sensitive mammalian mutant cells exhibiting sensitivity to a DNA-damaging agent, from resistant mammalian cells exhibiting resistance to said DNA-damaging agent, comprising the steps of:

growing a first population of clonal spheroids containing said resistant and sensitive mammalian mutant cells;

sorting said first population of clonal spheroids to obtain a second population of clonal spheroids of a first uniform size;

exposing said second population of clonal spheroids to said DNA-damaging agent;

growing said second population of clonal spheroids to form a third population of clonal spheroids comprising spheroids of increased size formed from said resistant mammalian cells and spheroids of substantially said first uniform size formed from said sensitive mammalian mutant cells;

flow sorting said third population of clonal spheroids by size to output first differentiated spheroids formed from said resistant mammalian cells and second differentiated spheroids formed from said sensitive mammalian mutant cells; and recovering sensitive mammalian mutant cells that survive in said second differentiated spheroids.

2. A method according to claim 1 wherein the step of growing a first population of clonal spheroids includes the step of subjecting a selected mammalian cell line to a mutagen to form a cell population containing both said resistant and sensitive mammalian mutant cells.

3. A method according to claim 1, wherein the step of recovering said surviving sensitive mammalian mutant cells that survive includes the step of culturing said second differentiated spheroids formed from said sensitive mammalian mutant cells to grow a population of sensitive mammalian mutant cells.

4. A method according to claim 1, wherein said step of recovering said surviving sensitive mammalian mutant cells that survive includes the step of dissociating said second differentiated spheroids formed from said sensitive mammalian mutant cells to single cell suspensions and growing sensitive mammalian mutant cell populations by cloning said single cell suspensions.

5. A method according to claim 3, further including the step of determining the sensitivity of said population of sensitive mammalian mutant cells to said DNA-damaging agent.

6. A method according to claim 4, further including the step of determining the sensitivity of said populations of sensitive mammalian mutant cells to said DNA-damaging agent.

* * * * *